United States Patent
Kuroda et al.

(10) Patent No.: US 8,991,610 B2
(45) Date of Patent: Mar. 31, 2015

(54) INDIVIDUALLY PACKAGED PRODUCT COMPRISING FIRST INDIVIDUAL PACKAGE, SECOND INDIVIDUAL PACKAGE AND ATTACHED PART

(75) Inventors: Kenichiro Kuroda, Kanonji (JP); Ranida Konthieng, Chachoengsao (TH)

(73) Assignee: Unicharm Corporation, Shikokuchuo-shi (JP)

( * ) Notice: Subject to any disclaimer, the term of this patent is extended or adjusted under 35 U.S.C. 154(b) by 369 days.

(21) Appl. No.: 13/508,251
(22) PCT Filed: Nov. 2, 2010
(86) PCT No.: PCT/JP2010/069867
§ 371 (c)(1), (2), (4) Date: Jun. 21, 2012
(87) PCT Pub. No.: WO2011/055828
PCT Pub. Date: May 12, 2011

(65) Prior Publication Data
US 2012/0255881 A1  Oct. 11, 2012

(30) Foreign Application Priority Data
Nov. 4, 2009  (JP) .................................. 2009-253484

(51) Int. Cl.
*B65D 69/00* (2006.01)
*A61F 13/551* (2006.01)
(52) U.S. Cl.
CPC ......... *A61F 13/5514* (2013.01); *A61F 13/5519* (2013.01)
USPC ............... 206/581; 206/38; 206/440; 53/443; 604/385.06
(58) Field of Classification Search
USPC ........... 206/38, 216, 438, 440, 581, 812, 823; 53/446, 445, 461; 604/385.02–385.06
See application file for complete search history.

(56) References Cited

U.S. PATENT DOCUMENTS 4,738,678 A * 4/1988 Paulis .................... 604/385.201
5,607,737 A * 3/1997 Blackwell et al. ............ 206/484
(Continued)

FOREIGN PATENT DOCUMENTS

EP  1 407 738  4/2004
EP  1 600 131  11/2005
(Continued)

OTHER PUBLICATIONS

International Search Report mailed Jan. 18, 2011, directed to International Application No. PCT/JP2010/069867; 2 pages.
(Continued)

*Primary Examiner* — Luan K Bui
(74) *Attorney, Agent, or Firm* — Morrison & Foerster LLP

(57) ABSTRACT

An individually packaged product is provided with a first individual package, a second individual package and an attaching part. The first individual package includes an absorbent article and a packaging sheet that packages the absorbent article. The second individual package includes a wipe and a packaging that protects the wipe. The attaching part attaches the second individual package to the first individual package such that the attaching strength of the attaching part for the second individual package is greater than the attaching strength of the attaching part for the first individual package, and at least a portion of the attaching part remains on the second individual package side after the second individual package has been removed from the first individual package. At least a portion of the attaching part has adhesiveness after the second individual package has been removed from the first individual package.

12 Claims, 7 Drawing Sheets

(56) References Cited

U.S. PATENT DOCUMENTS

| | | | |
|---|---|---|---|
| 5,683,377 A | 11/1997 | Mizutani | |
| 5,792,131 A | 8/1998 | Mizutani | |
| 6,911,022 B2* | 6/2005 | Steger et al. | 604/385.05 |
| 8,141,711 B2* | 3/2012 | Perry | 206/581 |
| 2003/0102239 A1* | 6/2003 | Beard | 206/440 |
| 2006/0275584 A1* | 12/2006 | Mori et al. | 428/156 |
| 2007/0142811 A1* | 6/2007 | Lais | 604/385.06 |
| 2008/0027405 A1* | 1/2008 | Hernandez et al. | 604/385.02 |
| 2008/0269710 A1 | 10/2008 | Caracci et al. | |
| 2008/0276570 A1 | 11/2008 | Kuroda et al. | |
| 2010/0078348 A1 | 4/2010 | Kondo et al. | |

FOREIGN PATENT DOCUMENTS

| | | |
|---|---|---|
| FR | 2 778 568 | 11/1999 |
| JP | 9-10257 | 1/1997 |
| JP | 9-10258 | 1/1997 |
| JP | 11-164849 | 6/1999 |
| JP | 2001-293028 | 10/2001 |
| JP | 2003-175990 | 6/2003 |
| JP | 2006-280522 | 10/2006 |
| JP | 2008-259583 | 10/2008 |
| JP | 4191596 | 12/2008 |
| JP | 2009-518248 | 5/2009 |
| WO | WO-93/21878 | 11/1993 |
| WO | WO-02/094149 | 11/2002 |
| WO | WO-2007/069218 | 6/2007 |

OTHER PUBLICATIONS

Extended European Search Report dated Dec. 12, 2013, directed to EP Application No. 10828386.2; 6 pages.

* cited by examiner (a)

(b)

INDIVIDUALLY PACKAGED PRODUCT COMPRISING FIRST INDIVIDUAL PACKAGE, SECOND INDIVIDUAL PACKAGE AND ATTACHED PART

REFERENCE TO RELATED APPLICATIONS

This application is the national stage under 35 USC 371 of International Application No. PCT/JP2010/069867, filed Nov. 2, 2010, which claims priority from Japanese Patent Application No. 2009-253484, filed Nov. 4, 2009, the entire contents of which are incorporated herein by reference.

FIELD OF THE INVENTION

The present invention relates to an individually packaged product provided with a first individual package, a second individual package and an attaching part.

BACKGROUND OF THE INVENTION

Individually packaged absorbent articles are conventionally known which have absorbent articles, such as sanitary napkins, panty liners and paper diapers wrapped in individual packaging sheets. Individual packaging of the absorbent articles allows each of the absorbent articles to be conveniently and hygienically carried.

There are also known individually packaged absorbent articles in which a wiping article, such as a wipe, is adhered, as described in PTL 1. Adhesion of a wipe to the individually packaged absorbent article is convenient as it allows wiping of soiled areas with the wipe when the absorbent article, such as a sanitary napkin, is exchanged.

As regards the individually packaged absorbent article of PTL 1, the connection relationship (connecting means) between the first member containing the absorbent article and the second member containing the wipe is merely described as being either permanent or temporary, as stated in paragraph [0011] of PTL 1, and the design does not take into account the conditions at the time of use of the individually packaged absorbent article.

In most cases where an absorbent article, such as a sanitary napkin is exchanged, it is a common procedure that the individually packaged sanitary napkin is opened and the fresh sanitary napkin is separated from the packaging sheet while the used sanitary napkin is affixed to the same packaging sheet, the used sanitary napkin then being wrapped up by the packaging sheet.

However, when a wipe is adhered to an individually packaged sanitary napkin, the wipe interferes during wrapping, such that it is necessary to pull off the wipe from the packaging sheet beforehand.

PATENT LITERATURE

[PTL 1] Japanese Unexamined Patent Publication No. 2009-518248

SUMMARY OF THE INVENTION

Thus, when it is attempted to use the individually packaged absorbent article described in PTL 1, which is not designed in consideration of the conditions during time of use, the wipe must be placed on a shelf or the like after it has been removed from the packaging sheet of the sanitary napkin, or when a shelf is not available or the available shelf is not hygienic, it is necessary to continue to hold the removed wipe with a hand so that it does not fall during exchange of the sanitary napkin, thus making it difficult or time-consuming to correctly fit the sanitary napkin.

It is therefore an object of the present invention to provide an individually packaged product that allows a removed second individual package to be adhered to a wall, door, clothing or the like, thus freeing both hands and facilitating exchange of the absorbent article.

As a result of diligent research directed toward solving the problems described above, the present inventors have found that the problems can be solved by an individually packaged product provided with a first individual package, a second individual package and an attaching part, wherein the first individual package comprises an absorbent article and a packaging sheet that packages the absorbent article, the second individual package comprises a wipe and a packaging that protects the wipe, the attaching part attaches the second individual package to the first individual package such that the attaching strength of the attaching part for the second individual package is greater than the attaching strength of the attaching part for the first individual package, and at least a portion of the attaching part remains on the second individual package side after the second individual package has been removed from the first individual package, with at least a portion of the attaching part having adhesiveness after the second individual package has been removed from the first individual package, and the present invention has been completed upon this finding.

Specifically, the present invention relates to the following aspects.

An individually packaged product provided with a first individual package, a second individual package and an attaching part, wherein the first individual package comprises an absorbent article and a packaging sheet that packages the absorbent article, the second individual package comprises a wipe and a packaging that protects the wipe, the attaching part attaches the second individual package to the first individual package such that the attaching strength of the attaching part for the second individual package is greater than the attaching strength of the attaching part for the first individual package, with at least a portion of the attaching part remaining on the second individual package side after the second individual package has been removed from the first individual package, and at least a portion of the attaching part has adhesiveness after the second individual package has been removed from the first individual package.

The individually packaged product according to aspect 1, wherein at least 50 mass % of the attaching part remains on the second individual package side after the second individual package has been removed from the first individual package.

The individually packaged product according to aspect 1 or 2, wherein the section of the first individual package in contact with the attaching part includes a concavoconvex section.

The individually packaged product according to any one of aspects 1 to 3, wherein the section of the second individual package in contact with the attaching part includes a concavoconvex section, and the attaching part is a hot-melt adhesive.

An individually packaged product according to any one of aspects 1 to 4, which is further provided with a release section, between the attaching part and the first individual package.

An individually packaged product according to any one of aspects 1 to 5, wherein the section of the second individual package in contact with the attaching part is a corona discharge treated section.

An individually packaged product according to any one of aspects 1 to 6, wherein the attaching part comprises the hook section of a mechanical fastener, the packaging sheet is a sheet comprising a loop section, and the attaching part attaches the second individual package to the first individual package through a connection between the hook section and the loop section.

The individually packaged product according to any one of aspects 1 to 7, wherein the packaging is a pillow-type packaging having a tab, formed by sealing together both edge regions of a roughly rectangular packaging material together to form a tubular body such that a tab is formed, and sealing both sides of the tubular body.

The individually packaged product according to aspect 8, wherein the tab is on the side of the second individual package opposite the first individual package.

The individually packaged product according to aspect 9, wherein the tab contains a weakened line or notched line which allows the wipe to be easily removed.

The individually packaged product according to aspect 8, wherein the tab is on the side of the second individual package facing the first individual package, the facing side is divided into two regions, with the tab overlapping one of the two regions, and the second individual package contacts with the attaching part within the region formed by the outer face of the tab and the other region of the two regions.

The individually packaged product according to any one of aspects 1 to 11, wherein the absorbent article is selected from the group consisting of sanitary napkins, panty liners, labial pads, paper diapers and tampons.

A method for producing an individually packaged product according to aspect 3 or 4, comprising the steps of:

applying the attaching part to the second individual package, and attaching the section of the first individual package comprising a concavoconvex section to the attaching part.

A method for producing an individually packaged product according to any one of aspects 1 to 6, in which the attaching part is a pressure-sensitive double-sided adhesive tape, comprising the steps of:

applying the attaching part to the second individual package by a first pressure, and attaching the attaching part to the first individual package by a second pressure that is lower than the first pressure.

The individually packaged product of the present invention allows a removed second individual package to be adhered to a wall, door, clothing or the like, thus freeing both hands and facilitating exchange of the absorbent article.

Also, with the individually packaged product of the present invention, at least a portion of the attaching part remains on the second individual package side after the second individual package has been removed from the first individual package, and therefore the second individual package can be used as a fastener when the used absorbent article is wrapped with a packaging sheet and discarded.

DETAILED DESCRIPTION OF THE INVENTION

The individually packaged product of the present invention will now be explained in detail with reference to the accompanying drawings where necessary.

Figure 1:
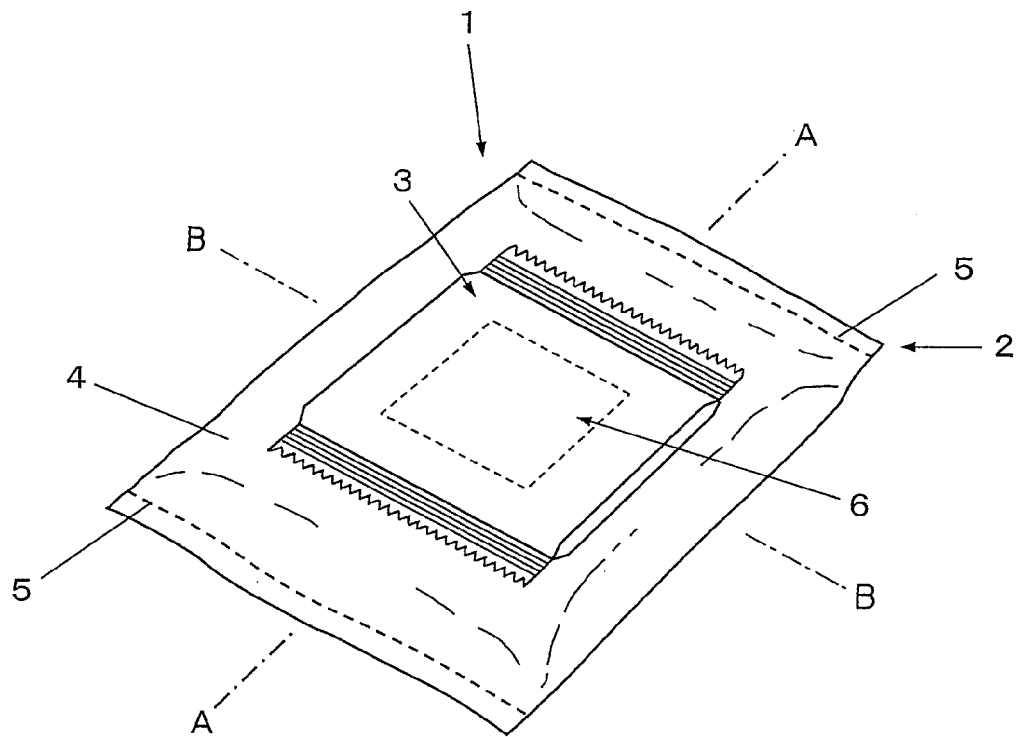
FIG. 1 is a perspective view of one embodiment of the individually packaged product of the present invention.
Figure 2:
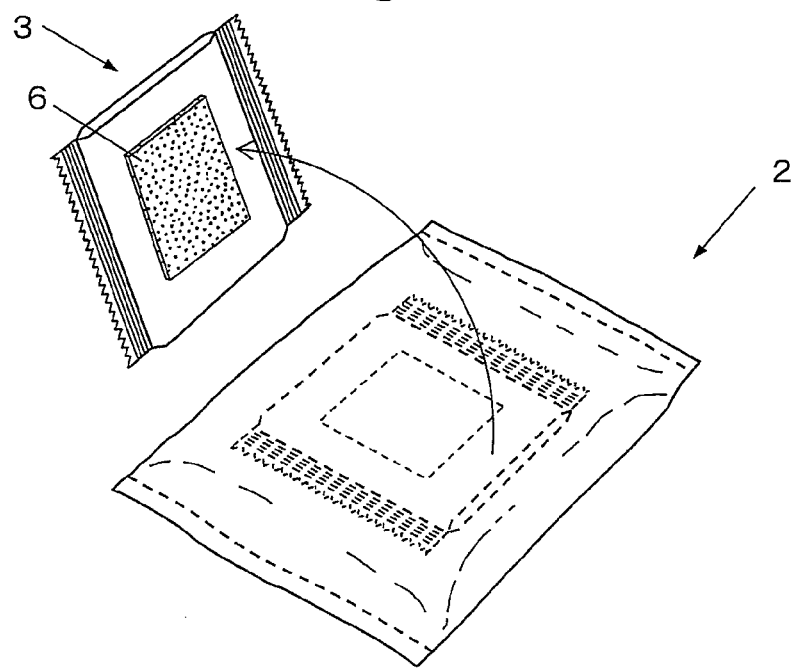
FIG. 2 is a drawing illustrating the use of the individually packaged product of the present invention.

FIG. 1 is a perspective view of one embodiment of the individually packaged product of the present invention, and FIG. 2 is a drawing illustrating the use of the individually packaged product of the present invention.

In the individually packaged product 1 shown in FIG. 1, the second individual package 3 is attached to the first individual package 2 by the attaching part 6. When the second individual package 3 is removed from the first individual package 2, at least a portion of the attaching part 6 remains on the second individual package 3 side, as shown in FIG. 2. Thus, the removed second individual package 3 is adhered to the toilet wall or door or to clothing using the attaching part 6, and both of the freed hands may be used to exchange the absorbent article.

In FIG. 1, numeral 4 denotes the packaging sheet of the first individual package 2, and numeral 5 denotes the seal line.

Figure 3:
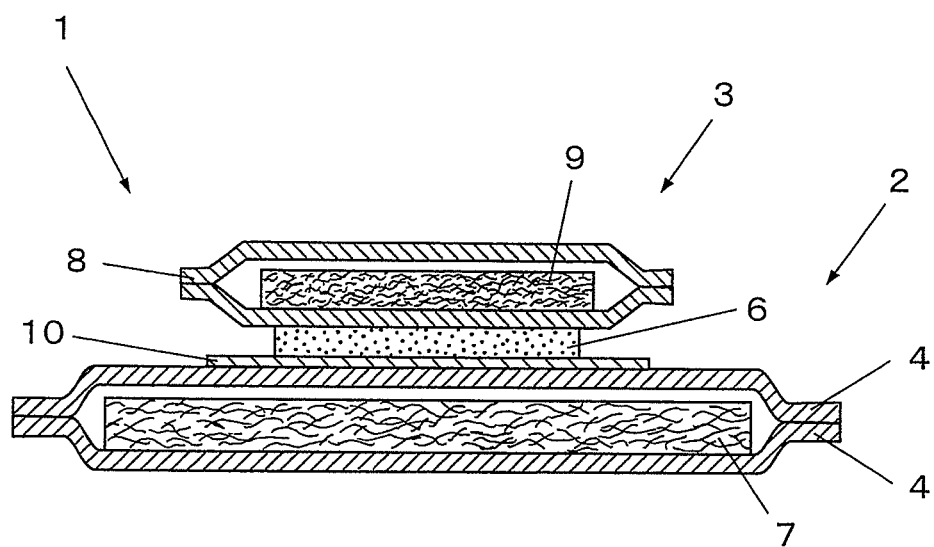
FIG. 3 is a cross-sectional view of one embodiment of the individually packaged product of the present invention.

FIG. 3 is a cross-sectional view showing one embodiment of the individually packaged product of the present invention, as a cross-sectional view corresponding to direction A-A in FIG. 1. In the individually packaged product 1 shown in FIG. 3, the second individual package 3 is attached to the first individual package 2 by the attaching part 6. In the first individual package 2, the absorbent article 7 is wrapped by the packaging sheet 4, and in the second individual package 3, the wipe 9 is wrapped by the packaging 8.

In the individually packaged product 1 shown in FIG. 3, a release section 10 is present between the attaching part 6 and the first individual package 2, and therefore the attaching strength of the attaching part 6 for the second individual package 3 is higher than the attaching strength of the attaching part 6 for the first individual package 2, and at least a portion of the attaching part 6 remains on the second individual package 3 side after the second individual package 3 has been removed from the first individual package 2.

The embodiment shown in FIG. 3 can be freely combined with other embodiments described herein.

In the present invention, preferably at least 50 mass % of the attaching part remains on the first individual package side, more preferably at least 80 mass % of the attaching part remains on the first individual package side, and even more preferably at least 90 mass % of the attaching part remains on the first individual package side, after the second individual package has been removed from the first individual package.

The absorbent article in the first individual package is not particularly restricted so long as it can be sold in a form that is individually packaged by a packaging sheet, and as examples there may be mentioned a sanitary napkin, panty liner, labial pad, paper diaper or tampon. The packaging sheet of the first individual package is also not particularly restricted so long as it can be used in the relevant technical field for individual packaging, and there may be mentioned woven fabrics, nonwoven fabrics, felts, piles, films, sheets and laminates. When the absorbent article is a sanitary napkin, panty liner or the like, a packaging sheet release-treated with silicone, for example, may be used in order to protect the adhesive sections that serve to adhere the absorbent article to shorts.

First individual packages wherein the absorbent article is a sanitary napkin may be the sanitary napkin packages described in Japanese Unexamined Patent Publication No. 9-10257, Japanese Unexamined Patent Publication No. 9-10258, Japanese Unexamined Patent Publication No. 2003-175990 and Japanese Unexamined Patent Publication No. 2006-280522, used without modification.

A first individual package wherein the absorbent article is a tampon may be the one described in Japanese Unexamined Patent Publication No. 2008-259583, used without modification.

A first individual package wherein the absorbent article is a labial pad may be the one described in International Patent Publication No. WO2002/094149.

The wipe used in the present invention is not particularly restricted and may be suitably used, so long as it is commonly used as a wipe in the technical field. The wipe used in the present invention may be a dry type or wet type. The material of the wipe may be a nonwoven fabric or woven fabric composed of hydrophilic fiber or a mixture of hydrophilic fiber and non-hydrophilic fiber. As hydrophilic fibers there may be mentioned regenerated cellulose fiber, such as rayon or natural fiber, such as cotton or pulp, and as non-hydrophilic fiber there may be mentioned polyester or polypropylene.

Considering that the wipe is to be flushed through the toilet after use, it preferably has water disintegratability, and is most preferably a nonwoven fabric with water disintegratability.

A binder may be added to the wipe to further increase the wet strength. As examples of binders there may be mentioned alkylcelluloses, such as carboxymethylcellulose, methylcellulose, ethylcellulose and benzylcellulose, as well as polyvinyl alcohols, modified polyvinyl alcohols containing prescribed amounts of sulfonic acid or carboxyl groups, and polyamide-epichlorhydrin.

When the wipe is a wet type, and the material is composed of a mixture of hydrophilic fiber and non-hydrophilic fiber, the proportion of hydrophilic fiber is preferably at least 40 mass % based on the total fiber mass. This will allow the wipe to retain a chemical solution, as explained below.

The wipe preferably has a basis weight of 20-100 $g/m^2$ from the viewpoint of ease of use.

When the wipe is a wet type, the wipe may contain a chemical solution at 100-500 mass % with respect to the mass of the wipe. Such a chemical solution may be a mixture of a minimal necessary amount of an antiseptic agent in purified water. The chemical solution may also contain, as necessary, various additives used in the technical field, such as one or more surfactants, humectants, refreshers, emollients, pH regulators, aromas, antioxidants, chelating agents, plant extracts, anti-browning agents, antiphlogistics, skin activators, astringents and tactile improvers.

The form of the packaging protecting the wipe is not particularly restricted so long as it is able to protect the wipe within it, and it may be a pillow-type package, three-way seal package, four-way seal package, or the like.

As used herein, "pillow-type package" is a package formed by rolling the packaging material into a circular cylinder and sealing both edges. It also includes the "pillow-type package having a tab", as described below. A "three-way seal package" is a package formed by folding the packaging material in two and sealing the three sides other than the folded-in-two section. A "four-way seal package" is a package formed by stacking two packaging materials and sealing the four sides.

The material of the packaging that protects the wipe is not particularly restricted and may be appropriately selected as one that is commonly used for packaging in the technical field, such as polyester, polypropylene or polyethylene terephthalate films, aluminum foil, paper or the like, either as a single layer or multiple layers. In a three-way seal package or four-way seal package described above, the seal sections may be formed by melt bonding of the film sections with heat or ultrasonic waves, or by using a hot-melt adhesive for bonding as described below.

The attaching part may be any attaching means commonly used in the technical field, without restrictions, and as examples there may be mentioned adhesives, double-sided adhesive tapes and the like. The aforementioned adhesives include pressure-sensitive adhesives, and the aforementioned double-sided adhesive tapes include pressure-sensitive double-sided adhesive tapes.

The adhesive may be any hot-melt adhesive commonly used in the technical field, without any particular restrictions. Hot-melt adhesives used in the technical field generally include thermoplastic polymers, tackifying resins, plasticizers, antioxidants, ultraviolet absorbers and the like. The aforementioned tackifying resins are components that impart not only adhesion during melting of the hot-melt adhesive but also adhesion after cooling, and the plasticizers are components that improve the hot flow property while also imparting flexibility to the hot-melt adhesive after cooling.

Since hot-melt adhesives commonly used in the technical field include the aforementioned tackifying resins and/or plasticizers, it is possible to maintain a constant attaching strength after cooling, for example, even after the second individual package has been removed from the first individual package.

Examples of the aforementioned thermoplastic polymers include synthetic rubber, such as SIS, SBS, SEPS or SEBS, EVA, and polyolefins, such as PE- or PP-based polymers, examples of the aforementioned tackifying resins include natural resins, such as rosin-based resins and terpene-based resins and synthetic resins, such as petroleum resins, and examples of the aforementioned plasticizers include paraffin-based oils, naphthene-based oils, natural waxes and synthetic waxes.

Examples of the aforementioned hot-melt adhesives include polyolefin (such as polyethylene and polypropylene)-based hot-melt adhesives, ethylene/vinyl acetate copolymer-based hot-melt adhesives, synthetic rubber (such as styrene-based polymer, butadiene-based polymer and isoprene-based polymer)-based hot-melt adhesives and acrylic resin-based pressure-sensitive adhesives.

Also, the aforementioned pressure-sensitive adhesives and pressure-sensitive double-sided adhesive tapes undergo minimal loss of adhesive force with time, and therefore at least a portion of the attaching part can retain a constant adhesive force after the second individual package has been removed from the first individual package.

As pressure-sensitive double-sided adhesive tapes that can be used in the present invention, there may be used pressure-sensitive double-sided adhesive tapes commonly used in the technical field, without any particular restrictions, and examples thereof include ATG Adhesive Transfer Tape 924 sold by Sumitomo-3M.

The release section may be a mold release sheet commonly used in the technical field. Examples of mold release sheets include sheets with low surface energy, such as sheets coated with silicone-based compounds, fluorine-based compounds or the like, and Teflon® sheets. Using a sheet with low surface energy can lower the attaching strength of the attaching part for the first individual package.

The release section may also be part of the packaging sheet of the first individual package, that has been release-treated. For example, the section of the packaging sheet surface with reduced surface energy, such as the section coated with a silicone-based compound or fluorine-based compound, is included in the packaging sheet section of the first individual package that has been release-treated.

Also the release section includes a section, such as a printed section, that releases with the attaching part and can lower the attaching strength of the attaching part for the first individual package. If the adhesive strength of the printed section for the first individual package is lower than the attaching strength of the attaching part for the first individual package, at least a portion of the attaching part will tend to remain on the second individual package after the second individual package has been removed from the first individual package.

When a printed section is used as the release section, the printed section is preferably provided on part of the surface of the first individual package that is in contact with the attaching part. This is because if the printed section is present on the entire surface of the first individual package in contact with the attaching part, the section which is not in contact with the second individual package, within the attaching part remaining on the second individual package side when the second individual package has been removed from the first individual package, will be entirely covered by the printed section and it will thus be difficult to adhere the second individual package to the wall, door, clothing or the like.

Figure 4:
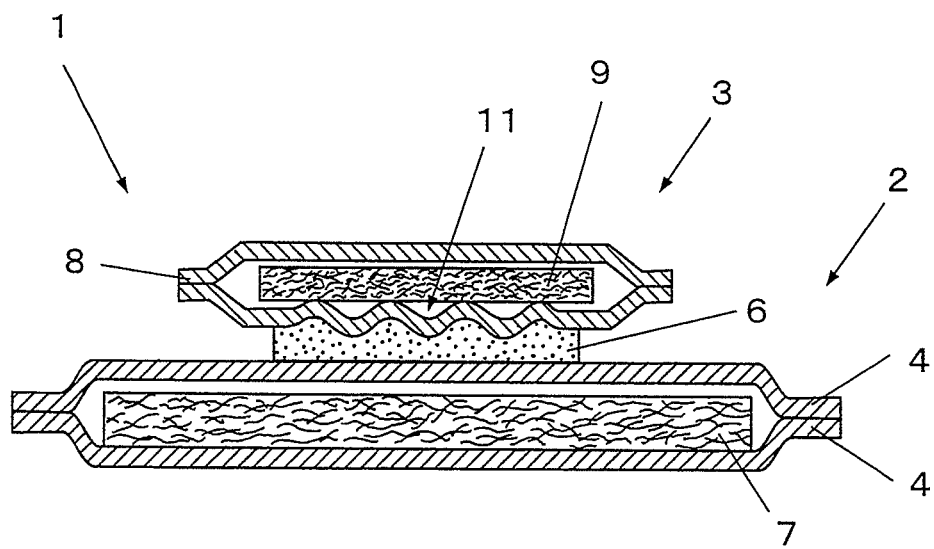
FIG. 4 is a cross-sectional view of one embodiment of the individually packaged product of the present invention.

FIG. 4 is a cross-sectional view of one embodiment of the individually packaged product of the present invention. FIG. 4 is also a cross-sectional view corresponding to direction A-A in FIG. 1. The individually packaged product 1 shown in FIG. 4 has a concavoconvex section 11 on at least a portion of the section of the second individual package 3 in contact with the attaching part 6, and it is produced by attaching the first individual package 2 to the attaching part 6 after the attaching part 6 has been applied to the section of the second individual package 3 containing the concavoconvex section 11, for example after the section of the second individual package 3 containing the concavoconvex section 11 has been coated with the attaching part 6.

In the individually packaged product 1 shown in FIG. 4, the second individual package contains a concavoconvex section 11 and the area of contact of the attaching part 6 with the second individual package 3 is larger than the area of contact of the attaching part 6 with the first individual package 2, and therefore the attaching strength of the attaching part 6 for the second individual package 3 is higher than the attaching strength of the attaching part 6 for the first individual package 2, and at least a portion of the attaching part 6 remains on the second individual package 3 side after the second individual package 3 has been removed from the first individual package 2.

The concavoconvex section 11 may be an embossed section, creased section, wrinkled section, or a scratched section formed by needles, but there is no limitation thereof.

In the individually packaged product 1 shown in FIG. 4, preferably the attaching part 6 is one that increases in viscosity or decreases in attaching force with time. This is because the attaching part or the material forming the attaching part in the individually packaged product 1 shown in FIG. 4 is applied (for example, coated) onto the second individual package and then applied (for example, affixed) onto the first individual package, and therefore when the attaching part or the material forming the attaching part is one that increases in viscosity with time, the contact area on the first individual package will tend to be smaller than the contact area on the second individual package.

The attaching part may be a hot-melt adhesive that decreases in temperature and increases in viscosity with time.

When a hot-melt adhesive is used as the attaching part, the hot-melt adhesive that has low viscosity at high temperature completely enters the recesses of the concavoconvex section when the hot-melt adhesive flows into the second individual package, to thus produce an anchoring effect. Also, when a woven fabric, nonwoven fabric or the like is used as the material of the packaging material for the second individual package, the hot-melt adhesive can enter between the fibers of the nonwoven fabric, thus producing a higher anchoring effect.

The attaching force of the hot-melt adhesive decreases to some extent after cooling. When a hot-melt adhesive is used as the attaching part, therefore, the adhesiveness after adhesion to a wall, door, clothing or the like is suitable and the hot-melt adhesive does not readily remain on the wall, etc., when removed.

The embodiment shown in FIG. 4 can be freely combined with other embodiments described herein.

Figure 5:
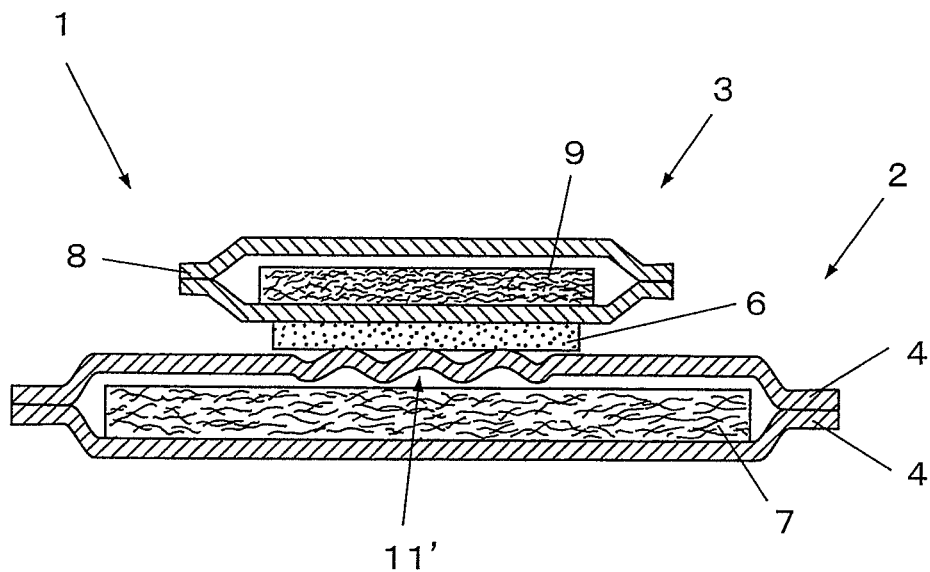
FIG. 5 is a cross-sectional view of one embodiment of the individually packaged product of the present invention.

FIG. 5 is a cross-sectional view of one embodiment of the individually packaged product of the present invention. FIG. 5 is also a cross-sectional view corresponding to direction A-A in FIG. 1. The individually packaged product 1 shown in FIG. 5 has a concavoconvex section 11' on at least a portion of the section of the first individual package 2 in contact with the attaching part 6, and it is produced by attaching the section of the first individual package 2 containing the concavoconvex section 11' to the attaching part 6, after the attaching part 6 has been applied to the second individual package 3, for example after the second individual package 3 has been coated with the attaching part 6.

Since the first individual package 2 in the individually packaged product 1 shown in FIG. 5 contains a concavoconvex section 11', the area of the attaching part 6 in contact with the first individual package 2, or the attaching strength of the attaching part 6 for the first individual package 2, is reduced when the attaching part used has increased viscosity or decreased attaching strength with time. Thus, at least a portion of the attaching part 6 remains on the second individual package side 3 after the second individual package 3 has been removed from the first individual package 2.

The concavoconvex section 11' may be an embossed section, creased section, wrinkled section, or a scratched section formed by needles. The material comprising the concavoconvex section 11' may be a woven fabric, nonwoven fabric, felt, pile, or any of these laminated with a polymer, such as polyethylene.

In the individually packaged product 1 shown in FIG. 5, preferably the attaching part 6 is one that increases in viscosity or decreases in attaching force with time, such as a hot-melt adhesive, for the same reason as the individually packaged product shown in FIG. 4.

The embodiment shown in FIG. 5 can be freely combined with other embodiments described herein.

Figure 6:
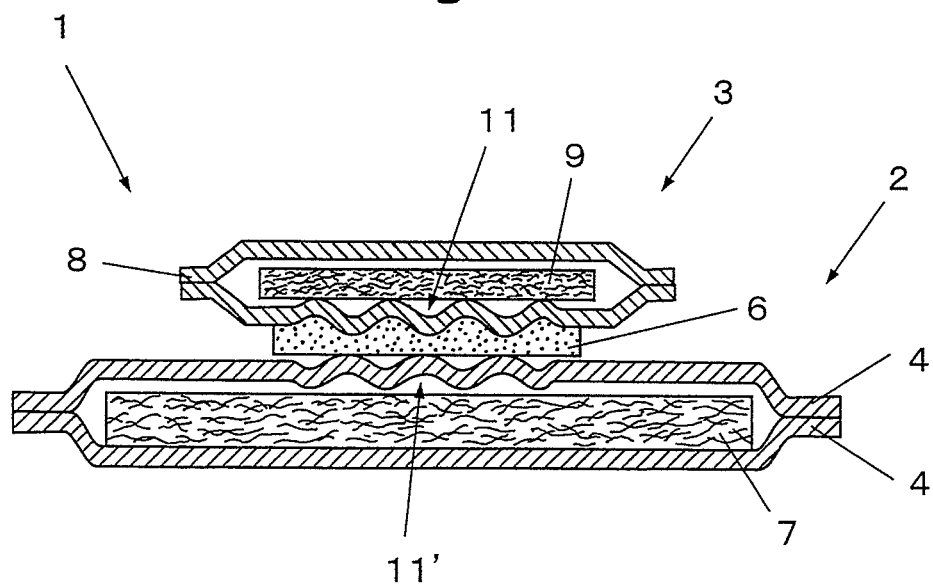
FIG. 6 is a cross-sectional view of one embodiment of the individually packaged product of the present invention.

FIG. 6 is a cross-sectional view of one embodiment of the individually packaged product of the present invention. FIG. 6 is a cross-sectional view corresponding to direction A-A in FIG. 1. The individually packaged product 1 shown in FIG. 6 has a concavoconvex section 11 on at least a portion of the section of the second individual package 3 in contact with the attaching part 6, as well as a concavoconvex section 11' on at least a portion of the section of the first individual package 2 in contact with the attaching part 6, and it is produced by attaching the section of the first individual package 2 containing the concavoconvex section 11' to the attaching part 6, after the attaching part 6 has been applied to the section of the second individual package 3 containing the concavoconvex section 11, for example after the section of the second individual package 3 containing the concavoconvex section 11 has been coated with the attaching part 6.

Employing the embodiment shown in FIG. 6 increases the difference between the attaching strength of the attaching part for the second individual package and the attaching strength of the attaching part for the first individual package, thus allowing more of the attaching part to remain on the second individual package side after the second individual package has been removed from the first individual package.

The embodiment shown in FIG. 6 can be freely combined with other embodiments described herein.

Figure 7:
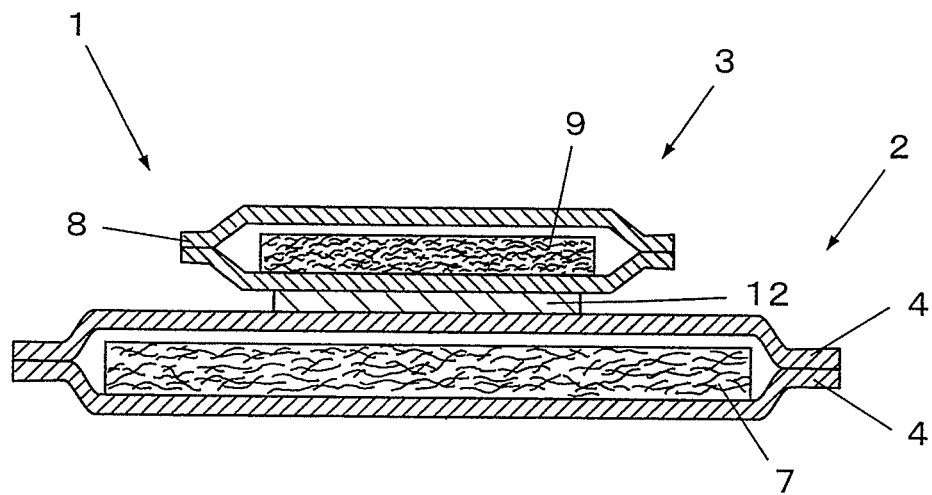
FIG. 7 is a cross-sectional view of one embodiment of the individually packaged product of the invention.

FIG. 7 is a cross-sectional view showing one embodiment of the individually packaged product of the present invention, and it is a cross-sectional view corresponding to direction A-A in FIG. 1. In the individually packaged product 1 shown in FIG. 7, the attaching part 6 is the hook section 12 of a mechanical fastener. The hook section 12 has a plurality of hooks on at least a portion of the section facing the first individual package 2. The packaging sheet 4 of the first individual package 2 is a sheet comprising a loop section containing a plurality of loops. The attaching part attaches the second individual package 3 to the first individual package 2 through connections between the hook section 12 and the loop section of the packaging sheet 4.

The mechanical fastener is a sheet-like fastener based on mechanical bonding, and for example, it may be a combination of a hook section having a plurality of, for example, hook-shaped, mushroom-shaped or anchor-shaped protrusions formed on the surface, and a loop section having a plurality of loops arranged on the surface. The mechanical fastener can attach two members in a releasable manner, by engaging the plurality of hooks of the hook section with the plurality of loops of the loop section.

The hook section 12 may be one that is commonly used in the field of paper diapers and the like. The sheet with a loop section may be a woven fabric, nonwoven fabric, felt, pile or the like.

The attaching part has a hook section at least on the surface facing the first individual package, while the surface of the attaching part facing the second individual package may be any attaching means disclosed herein, such as a hook section, hot-melt adhesive or pressure-sensitive double-sided adhesive tape.

For example, when the surface of the attaching part facing the second individual package has a hook section, the packaging of the second individual package has a loop section, and the number of hooks in the hook section on the surface facing the second individual package is preferably greater than the number of hooks in the hook section on the surface facing the first individual package. This is because the attaching strength of the attaching part for the second individual package is higher than the attaching strength of the attaching part for the first individual package.

Also, when the surface of the attaching part facing the second individual package is a pressure-sensitive double-sided adhesive tape, the pressure-sensitive double-sided adhesive tape is attached such that the attaching strength of the pressure-sensitive double-sided adhesive tape for the second individual package is higher than the attaching strength of the hook section between the loop section of the first individual package.

In the individually packaged product 1 shown in FIG. 7, the second individual package 3 removed from the first individual package 2 is preferably adhered to a section with loop sections, such as clothing or a towel.

The embodiment shown in FIG. 7 can be freely combined with other embodiments described herein.

Figure 8:
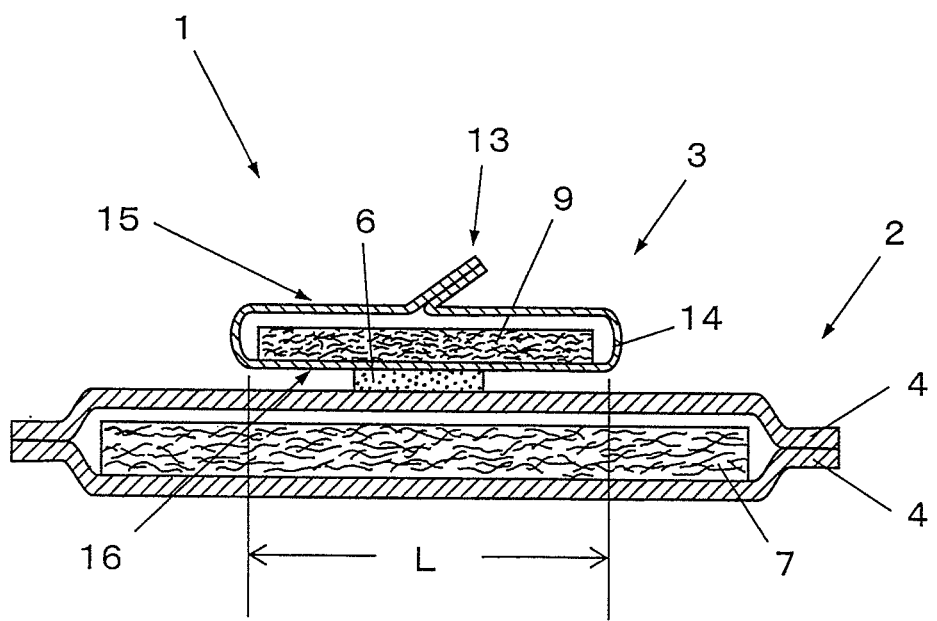
FIG. 8 is a cross-sectional view of one embodiment of the individually packaged product of the present invention.

FIG. 8 is a cross-sectional view showing one embodiment of the individually packaged product of the present invention, wherein the packaging of the second individual package is a pillow-type package having a tab. In the individually packaged product 1 of FIG. 8, the tab 13 is on the side 15 of the second individual package opposite the first individual package side. The pillow-type package 14 having a tab may be formed, for example, by sealing both edge regions of a roughly rectangular packaging material to form a tubular body with a tab, and sealing both sides of the tubular body.

In the individually packaged product 1 shown in FIG. 8, the tab 13 is on the side 15 of the second individual package opposite the first individual package side, and therefore the user can grip the tab 13 to easily remove the second individual package 3 from the first individual package 2.

Therefore, with the individually packaged product 1 shown in FIG. 8, the user can grip the tab 13 for easy removal of the second individual package 3 from the first individual package 2, even when the attaching part 6 contacts the entire side 16 of the second individual package facing the first individual package (that is, the region represented by L in the cross-sectional view of FIG. 8).

Also, since the tab 13 is on the side 15 of the second individual package opposite the first individual package side, it is possible, even after the second individual package 3 has been adhered to a wall, door, clothing or the like, for the user to grip the tab 13 for easy removal of the second individual package 3 from the wall, etc.

The user can also pull the tab to remove the wipe in the second individual package 3, while keeping the second individual package adhered to the wall, etc.

The embodiment shown in FIG. 8 can be freely combined with other embodiments described herein.

Figure 9:
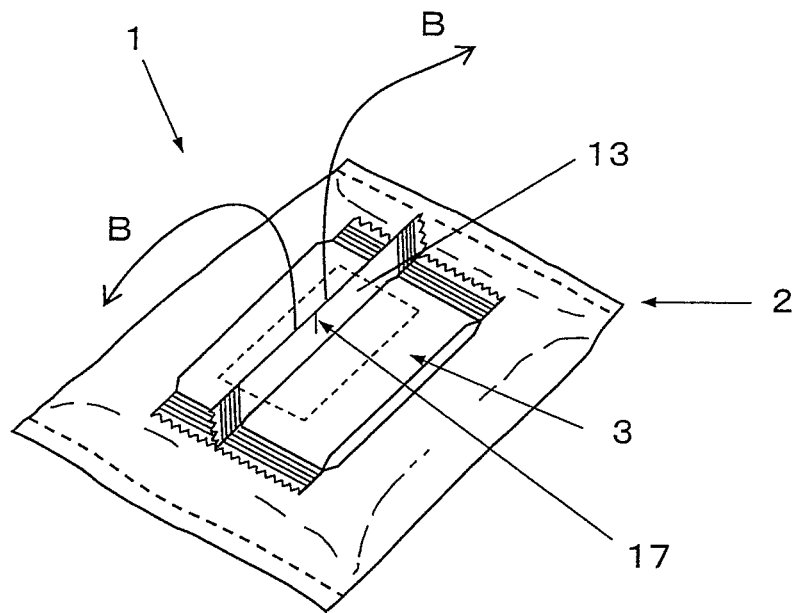
FIG. 9 is a perspective view illustrating a notched line provided on a tab.

FIG. 9 is a perspective view illustrating a notched line provided on a tab. The individually packaged product 1 shown in FIG. 9 has a notched line 17 provided on the tab 13, to allow easy removal of the wipe in the second individual package 3. The user can open the tab 13 from the notched line 17 in the direction indicated by B in the FIG. 9, while the second individual package 3 is adhered to a wall, door, clothing or the like.

A weakened line may also be provided instead of the notched line 17.

Figure 10:
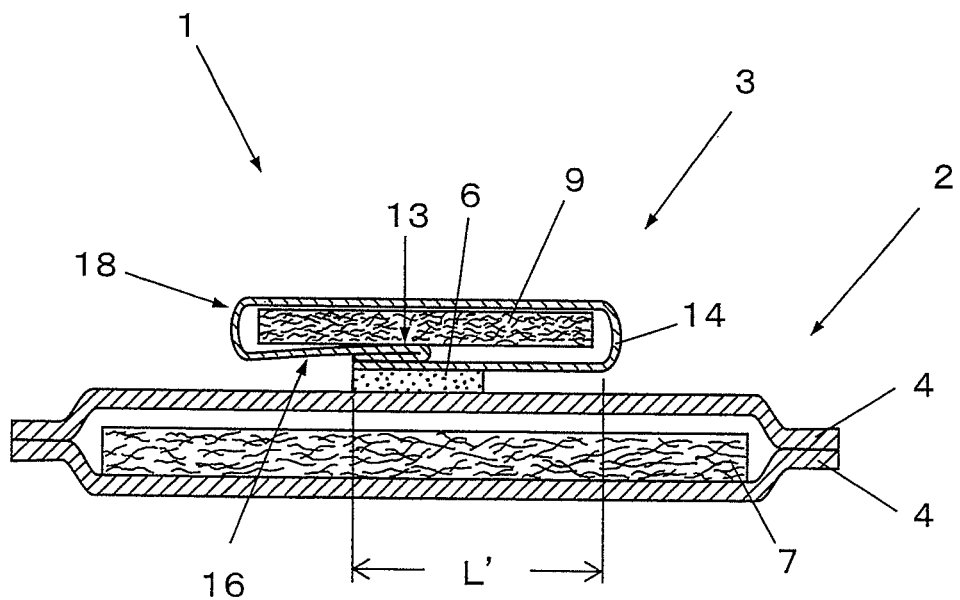
FIG. 10 is a cross-sectional view of one embodiment of the individually packaged product of the present invention.
Figure 11:
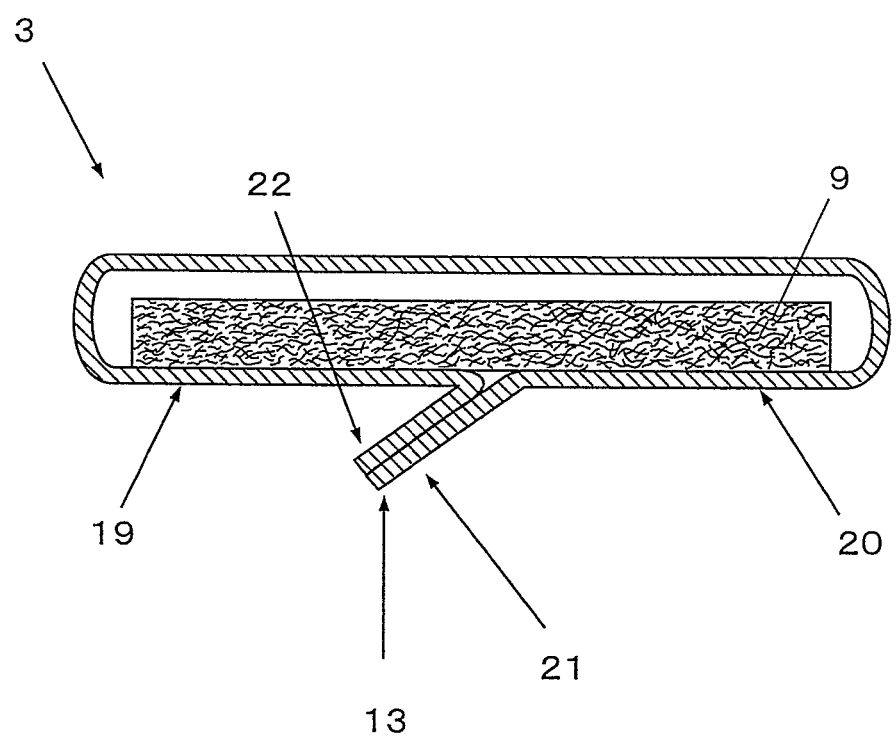
FIG. 11 is a drawing illustrating the second individual package 3 shown in FIG. 10.

FIG. 10 is a cross-sectional view showing one embodiment of the individually packaged product of the present invention, as an embodiment wherein the packaging of the second individual package is a pillow-type package having a tab, and the tab is on the side of the second individual package facing the first individual package. FIG. 11 is a drawing illustrating the second individual package 3 shown in FIG. 10.

In the embodiment of the individually packaged product 1 shown in FIG. 10, a free end (for example, the free end 18) is preferably provided on the second individual package 3, to facilitate removal of the second individual package 3 from the first individual package 2.

As an example of providing a free end on the second individual package 3, there may be mentioned an embodiment having at least the free end 18, wherein the second individual package 3 contacts with the attaching part 6 in a region composed of other region 20 and the outer face 21 of the tab (that is, in the region indicated by L' in the cross-sectional view of FIG. 10).

The other region 20 is a region on the side 16 of the second individual package facing the first individual package, wherein the tab 13 is not folded, of the two regions demarcated by the tab 13. The region on the side 16 of the second individual package facing the first individual package, wherein the tab 13 is folded, of the two regions demarcated by the tab 13, will be referred to as the first region 19.

The outer face 21 of the tab is the side of the tab 13 that is not facing the side 16 of the second individual package facing the first individual package (usually the opposite side). The inner face 22 of the tab is the side of the tab 13 that is facing the side 16 of the second individual package facing the first individual package.

With this embodiment, the user can grip the free end 18 to easily remove the second individual package 3 from the first individual package 2. It is also possible, even after the second individual package 3 has been adhered to a wall, door, clothing or the like, for the user to grip the free end 18 for easy removal of the second individual package 3 from the wall, etc.

The embodiment shown in FIG. 10 can be freely combined with other embodiments described herein.

Figure 12:
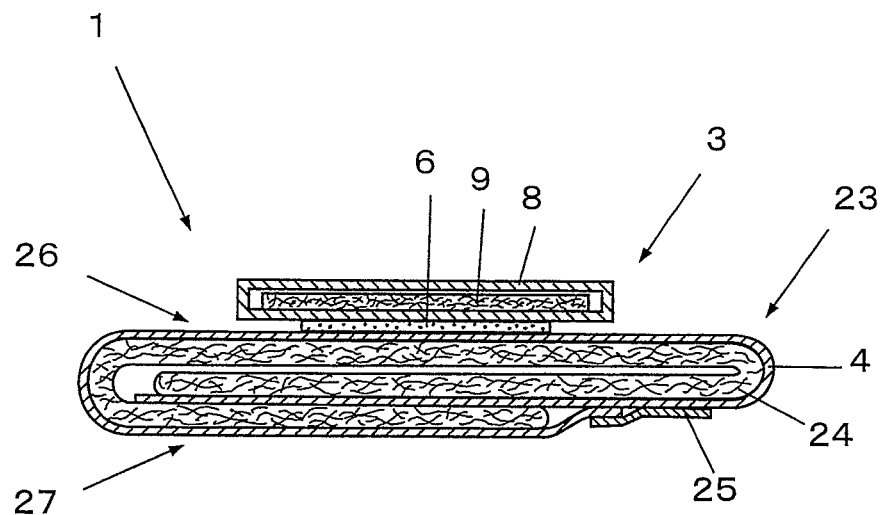
FIG. 12 is a cross-sectional view of one embodiment of an individually packaged product wherein the first individual package is an individually packaged sanitary napkin.
Figure 12:
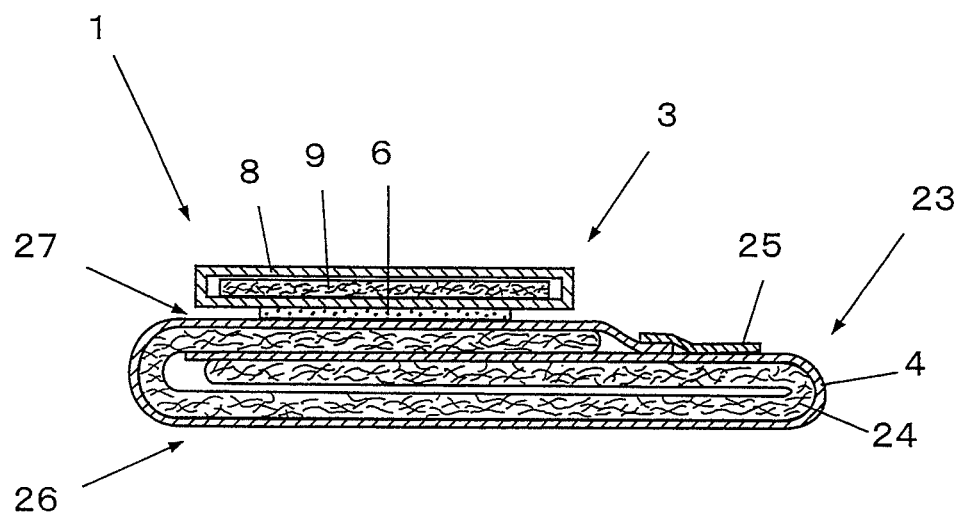

FIG. 12 is one embodiment of the individually packaged product of the present invention, as an example wherein the first individual package is an individually packaged sanitary napkin. FIG. 12 is a cross-sectional view corresponding to direction B-B in FIG. 1.

In FIG. 12(a), the second individual package 3 is attached to the individually packaged sanitary napkin 23 through the attaching part 6. In the individually packaged sanitary napkin 23, the sanitary napkin 24 is a folded-in-three type, wherein it is folded in three with the packaging sheet 4 and attached with the gripping tab 25. The second individual package 3 is attached to the unopen side 26 of the individually packaged sanitary napkin 23. As used herein, "unopen side" means the side of the packaging sheet that has no opening.

In FIG. 12(b), the second individual package 3 is attached to the open side 27 of the individually packaged sanitary napkin 23. As used herein, "open side" means the side of the packaging sheet that has an opening, allowing the absorbent article therein to be removed.

FIGS. 12(a) and (b) show an example where the first individual package is an individually packaged sanitary napkin, and there is no limitation to the shape of the individually packaged sanitary napkin, which includes, for example, types wherein the sanitary napkin is a folded-in-four type, or the packaging sheet, which may form a pillow-type package, three-way seal package, four-way seal package or the like.

Similarly, the second individual package 3 may be attached as shown in FIG. 12, even when the first individual package is an individually packaged panty liner, individually packaged labial pad, individually packaged paper diaper or individually packaged tampon. Also, forms of individually packaged panty liners, individually packaged labial pads, individually packaged paper diapers and individually packaged tampons include those wherein their packaging sheets form pillow-type packages, three-way seal packages, four-way seal packages and the like.

As one embodiment of the individually packaged product of the present invention, an individually packaged product may be obtained wherein pressure-sensitive double-sided adhesive tape is used as the attaching part such that the attaching strength of the attaching part for the second individual package is higher than the attaching strength of the attaching part for the first individual package, and so that at least a portion of the attaching part remains on the second individual package side after the second individual package has been removed from the first individual package.

For example, if the pressure-sensitive double-sided adhesive tape is affixed to the second individual package by a first pressure and then the pressure-sensitive adhesive is affixed to the first individual package with a second pressure that is lower than the first pressure, it is possible for the attaching strength of the attaching part for the second individual package to be higher than the attaching strength of the attaching part for the first individual package.

An embodiment employing such pressure-sensitive double-sided adhesive tape may be freely combined with other embodiments described herein.

Another embodiment of the individually packaged product of the present invention is one wherein the side of the second individual package in contact with the attaching part is subjected to corona treatment. Corona treatment increases the surface energy of the treated side so that the attaching strength of the attaching part for the second individual package is further increased, thus allowing more of the attaching part to remain on the second individual package side after the second individual package has been removed from the first individual package.

An embodiment employing such corona treatment may be freely combined with other embodiments described herein.

In each of the embodiments described above, the attaching strength of the attaching part for the first individual package is preferably in the range of 0.5N-5.0N and more preferably in the range of 1.0N-4.0N. Individually packaged products are usually kept in a bag, pouch or the like when carried away from home, and if the attaching strength is less than 0.5N the second individual package separates from the first individual package, undesirably adhering to various parts of the bag or pouch. In addition, repeated and frequent adhesion and removal causes the adhesiveness of the attaching part to decrease, making it difficult to perform adhesion to a wall, door, clothing or the like during use.

The attaching strength is also preferably not greater than 5.0N, because excessive force will be necessary to remove the second individual package from the first individual package.

In an embodiment employing a release section, as described above, the attaching strength of the attaching part for the release section is preferably in the range of 0.5N-5.0N and more preferably in the range of 1.0N-4.0N, for the same reason given above.

Measurement of the attaching strength is accomplished as follows: the first individual package and the second individual package are each gripped with a jig, and then a tensile tester (100 mm/min) is used to measure the force when the second individual package (more precisely, the attaching part) is pulled off from the first individual package. The force during pulling is recorded as the attaching strength.

The tensile tester used is, for example, a Single Column Test System, Model 3343 by Instron.

So long as the attaching strength of the attaching part for the second individual package is larger than the attaching strength of the attaching part for the first individual package, there is no particular limitation on the strength. The attaching strength of the attaching part for the second individual package is preferably a sufficiently greater value than the attaching strength of the attaching part for the first individual package. This is to allow at least a portion of the attaching part to remain on the second individual package side after the second individual package has been removed from the first individual package.

The areas of the attaching part attaching the first individual package and second individual package are preferably each at least 5%, more preferably at least 10% and even more preferably at least 20% of the area of the section of the second individual package facing the first individual package. If the area is less than 5%, the second individual package will tend to detach from the first individual package.

In an embodiment employing the release section described above, the area of the attaching part attaching the release section and the area of the release section attaching the first individual package are preferably each at least 5%, more preferably at least 10% and even more preferably at least 20% of the area of the section of the second individual package facing the first individual package.

In order to allow sufficient adhesion to a wall, door, clothing or the like after the second individual package has been removed from the first individual package, the second individual package removed from the first individual package preferably has adhesiveness, such as an adhering strength of at least 1.0N as measured by the test method described below.

The method of measuring the adhering strength is as follows: the second individual package that has been removed from the first individual package is placed on a #4 shirting with the attaching part facing downward, and then a 2 kg roller is passed once over the second individual package at a speed of 4 m/sec to adhere the second individual package onto the #4 shirting. A tensile tester (100 mm/min) is then used to measure the force at which the second individual package is removed from the #4 shirting, which is recorded as the adhering strength.

The tensile tester used is, for example, a Single Column Test System, Model 3343 by Instron.

REFERENCE SIGNS LIST

1 Individually packaged product
2 First individual package
3 Second individual package
4 Packaging sheet
5 Seal line
6 Attaching part
7 Absorbent article
8 Packaging
9 Wipe
10 Release section
11, 11' Concavoconvex sections
12 Hook section
13 Tab
14 Pillow-type package having a tab
15 Side of second individual package opposite first individual package side
16 Side of second individual package facing first individual package side
17 Notched line
18 Free end
19 First region
20 Other region
21 Outer face of tab
22 Inner face of tab
23 Individually packaged sanitary napkin
24 Sanitary napkin
25 Gripping tab
26 Unopen side
27 Open side

The invention claimed is:

1. An individually packaged product comprising a combination of a first individual package, and a second individual package, the first and second individual packages containing different contents, and being configured to be separated from each other before use thereof,
   wherein the first individual package comprises an absorbent article and a packaging sheet that packages the absorbent article,
   the second individual package comprises a wipe and a packaging that protects the wipe, and
   the individually packaged product further comprises an attaching part temporarily attaching the second individual package to the first individual package such that the attaching strength of the attaching part for the second individual package is greater than the attaching strength of the attaching part for the first individual package, and at least a portion of the attaching part remains on a side of the second individual package after the second individual package has been removed from the first individual package,
   wherein the individually packaged product comprises at least one member selected from the group consisting of:
   (i) a concavoconvex section provided to a section of the first individual package in contact with the attaching part so that the attaching strength of the attaching part for the second individual package is greater than the attaching strength of the attaching part for the first individual package;
   (ii) a concavoconvex section provided to a section of the second individual package in contact with the attaching part so that the attaching strength of the attaching part for the second individual package is greater than the attaching strength of the attaching part for the first individual package; and
   (iii) a release section positioned between the attaching part and the first individual package so that the attaching strength of the attaching part for the second individual package is greater than the attaching strength of the attaching part for the first individual package; and
   at least a portion of the attaching part has adhesiveness after the second individual package has been removed from the first individual package.

2. The individually packaged product according to claim 1, wherein at least 50% by weight of the attaching part remains on the side of the second individual package after the second individual package has been removed from the first individual package.

3. The individually packaged product according to claim 1, wherein the attaching part is a hot-melt adhesive.

4. The individually packaged product according to claim 1, wherein the section of the second individual package in contact with the attaching part is a corona discharge treated section.

5. The individually packaged product according to claim 1, wherein the attaching part comprises the hook section of a mechanical fastener, the packaging sheet is a sheet comprising a loop section, and the attaching part attaches the second individual package to the first individual package through a connection between the hook section and the loop section.

6. The individually packaged product according to claim 1, wherein the packaging is a pillow-type packaging having a tab, formed by sealing together both edge regions of a roughly rectangular packaging material together to form a tubular body such that the tab is formed, and sealing both sides of the tubular body.

7. The individually packaged product according to claim 6, wherein the tab is on the side of the second individual package opposite the first individual package.

8. The individually packaged product according to claim 7, wherein the tab contains a weakened line or notched line which allows the wipe to be easily removed.

9. The individually packaged product according to claim 6, wherein the tab is on the side of the second individual package facing the first individual package, the facing side is divided into two regions, with the tab overlapping one of the two regions, and the second individual package contacts with the attaching part within the region formed by the outer face of the tab and the other region of the two regions.

10. The individually packaged product according to claim 1, wherein the absorbent article is selected from the group consisting of sanitary napkins, panty liners, labial pads, paper diapers and tampons.

11. A method for producing the individually packaged product according to claim 1, comprising:

applying the attaching part to the second individual package, and attaching the section of the first individual package comprising the concavoconvex section to the attaching part.

12. A method for producing the individually packaged product according to claim 1, in which the attaching part is a pressure-sensitive double-sided adhesive tape, comprising:

applying the attaching part to the second individual package by a first pressure, and attaching the attaching part to the first individual package by a second pressure that is lower than the first pressure.

* * * * *